United States Patent [19]

Pope, Jr. et al.

[11] 4,284,505
[45] Aug. 18, 1981

[54] FLEXIBLE MEMBRANE FILTER ASSEMBLY

[75] Inventors: J. Lee Pope, Jr., Baltimore, Md.; James W. Scott, Lindenhurst, Ill.

[73] Assignee: Baxter Travenol Laboratories, Inc., Deerfield, Ill.

[21] Appl. No.: 89,601

[22] Filed: Oct. 29, 1979

[51] Int. Cl.³ .............................................. B01D 31/00
[52] U.S. Cl. .................................... 210/236; 210/356; 210/448; 210/462
[58] Field of Search ............... 210/356, 462, 448, 236, 210/346

[56] References Cited

U.S. PATENT DOCUMENTS

| | | | |
|---|---|---|---|
| 2,376,739 | 5/1945 | Walker, Jr. | 210/462 |
| 2,591,056 | 4/1952 | Ericson | 210/181 |
| 3,228,877 | 1/1966 | Mahon | 210/22 |
| 3,343,681 | 9/1967 | Madden | 210/356 X |
| 3,353,678 | 11/1967 | Dragon | 210/236 |

Primary Examiner—Frank A. Spear, Jr.
Attorney, Agent, or Firm—Paul C. Flattery; John P. Kirby, Jr.; Gary W. McFarron

[57] ABSTRACT

A membrane filter assembly is disclosed which employs at least one filter membrane and includes support means to prevent overflexing or overstressing of the filter membrane when high fluid pressures occur. The membrane support means includes a substantially co-extensive support or back-up surface spaced a small distance from the membrane to allow liquid flow therethrough but to prevent stretching or flexing beyond its elastic limit. Preferably the support surface comprises a second filter membrane in parallel flow relationship with the first to provide high flow rates during normal flow conditions but which flex together during high pressures conditions to mutually support one another and to prevent further flexure of either membrane beyond its elastic limit.

9 Claims, 6 Drawing Figures

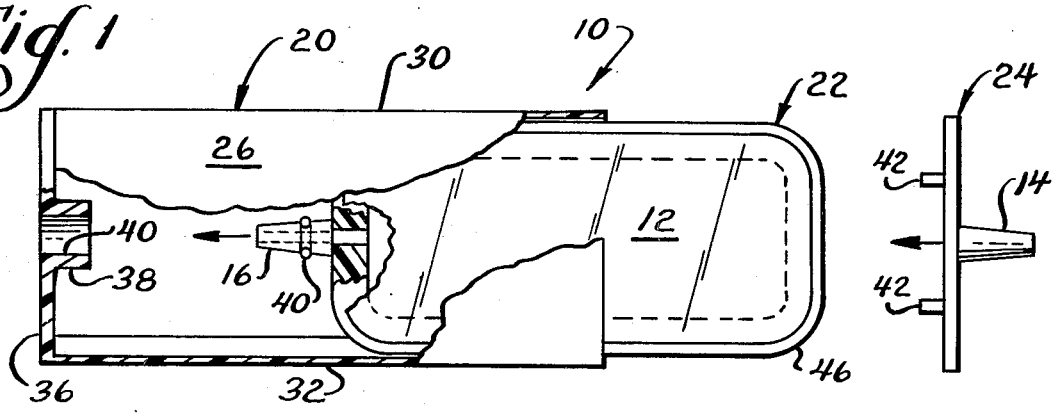
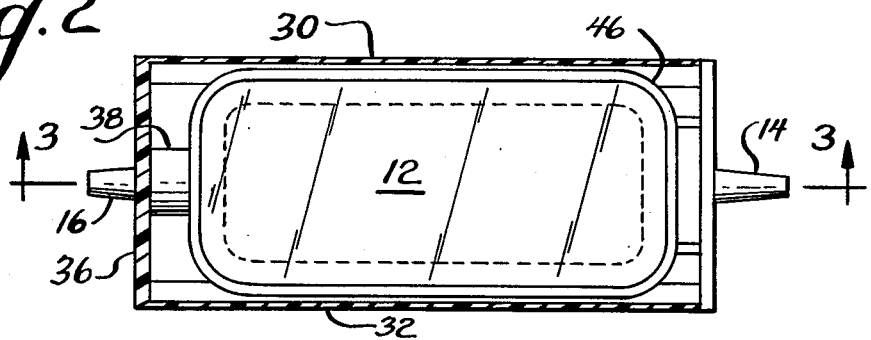
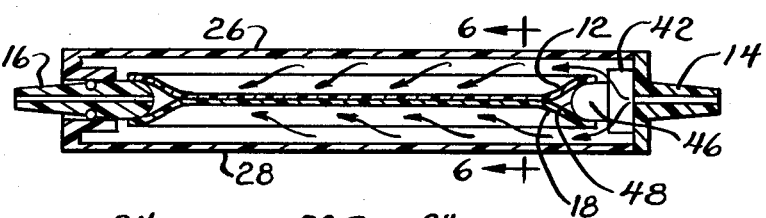
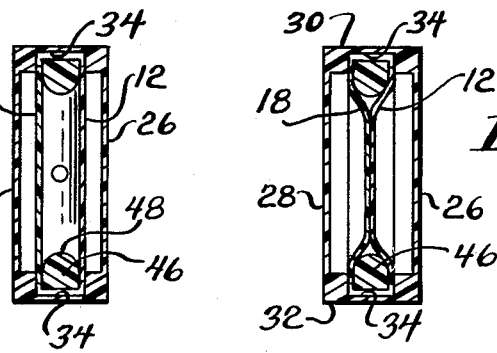
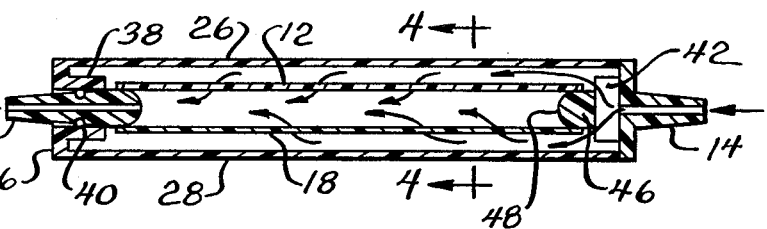

FLEXIBLE MEMBRANE FILTER ASSEMBLY

The present invention generally relates to filter assemblies which employ one or more microporous membranes for the filtration of fluids, particularly medical fluids such as parenteral solutions and the like. More specifically, it relates to membrane filter assemblies which have means for supporting the membranes against overflexing or stressing.

Microporous filter membranes with very small pore sizes, often less than about one micron, have been widely used in the medical field to remove microscopic particulate from medical fluids, such as parenteral solutions. These filters are frequently employed in intravenous administration sets to provide a final filtration before the solution is administered to the patient. Some examples of the wide variety of membrane filter assemblies found in the medical field are shown in one or more of the following U.S. Pat. Nos. 3,523,408; 3,631,654; 3,650,093; 3,803,810; 3,854,907; 3,954,623; 4,004,587; 4,009,714; 3,149,758; 3,778,971; 3,506,130; 3,905,905 and 4,009,715; French Pat. No. 2,314,753 and British Pat. No. 1,221,625.

Because the microporous membranes used in such filters are usually very thin and fragile, it is often necessary that precautions be taken to prevent excessive flexure or stretching of the membrane which may cause fracture, tearing or other failure of the membrane. This is particularly true in filter assemblies which may, from time to time, be subjected to relatively high pressures, e.g., by the injection of medication into the administration set from a syringe, which can create pressures of up to about 150 psi. In addition, intravenous fluid pumps, which are becoming increasingly important in parenteral nutritional therapy, may also be capable of generating relatively high pressure differentials across a filter membrane in the fluid administration line.

To prevent membrane failure under the conditions described above, filter assemblies have often included a support structure designed to prevent any flexure of the membrane or, at least, to minimize flexure. Compare, for example, the filter shown in U.S. patent application Ser. No. 016,027, filed Feb. 28, 1979, to Pope et al., which used a support screen as well as underlying ribs to reinforce the filter membrane. Although this filter functions satisfactorily, it requires additional assembly steps associated with the support screen. In addition, the need for a support structure may limit the size of the membrane used in the assembly, which limits the liquid flow rate through the filter assembly.

Accordingly, it is a general object of the present invention to provide an improved microporous membrane type filter assembly which can withstand relatively high pressures without the danger of rupturing or tearing the membrane from overflexure or overstressing.

It is a further object of the present invention to provide such a filter which does not require a complicated or complex support structure for reinforcing the membrane against high pressures.

It is still another object of the present invention to provide such a filter which is easy to manufacture and relatively inexpensive.

Another object of the present invention is to provide such a filter assembly that is resistant to high pressures but yet still provides a relatively large filter surface area for high volume flow of liquid through the filter assembly.

These and other objects of the present invention are set forth in the following detailed description of the preferred embodiment of the present invention, as shown in the attached drawings, of which:

FIG. 1 is a plan view of a filter assembly embodying the present invention, partially disassembled and partially in section.

FIG. 2 is a partial sectional view of the assembled filter of FIG. 1, with a membrane carrying insert member in plan view.

FIG. 3 is a vertical sectional view along line 3—3, the longitudinal axis of the assembled filter of FIG. 2, illustrating liquid under normal pressures passing through the filter assembly.

FIG. 4 is a vertial sectional view taken along line 4—4 of FIG. 3.

FIG. 5 is a vertical sectional view taken along the longitudinal axis of the assembly when relatively high pressure differential is applied across the filter membrane.

FIG. 6 is a vertial sectional view taken along line 6—6 of FIG. 5.

The present invention is generally embodied in a filter assembly 10 which employs at least one microporous filtering membrane 12 through which liquid must pass as it moves between an inlet 14 and outlet 16 of the filter assembly. In accordance with the present invention, a co-extensive support surface is spaced a small distance from filter membrane 12 to permit liquid flow therebetween under normal liquid flow pressures but to prevent the membrane from flexing beyond its elastic limit under higher than normal fluid pressures. That is, in marked contrast to prior reinforced filters, the membrane here is intentionally permitted to flex or stretch across the small spacing between the membrane and support surface, which spacing is within the membrane's elastic range. Thus, under high pressure, the membrane comes to rest substantially fully against the support surface, which is generally planar and prevents further flexure. In the preferred embodiment, as best seen in FIGS. 3-6, the filter assembly 10 includes a second microporous membrane 18 closely facing the membrane 12 and in parallel flow relationship therewith. Under normal pressure, a relatively high volume of filtering liquid can thus flow through the facing membranes to the outlet 16 which communicates between them, but when higher pressures occur, both membranes will flex or stretch one-half of the small distance between them until they rest substantially completely against one another, each providing a mutual co-extensive support surface for the other and preventing any further flexure. In addition, the bubble point of the normally hydrophilic filter membranes is preferably higher than the high pressures which may be encountered to prevent any gas or air from passing through the filter membranes to the patient.

Turning now to a more detailed description of the preferred embodiment of the present invention, as illustrated in the attached drawings, a filter in accordance with the present invention may be constructed of three easily assembled parts: an elongated outer sleeve or housing 20, a filter cartridge of insert member 22 receivable through an open end of the sleeve and a cap 24 to close and seal the open end of the sleeve. The sleeve, insert and cap are preferably of molded plastic construction and may be made of any material, e.g., acrylic or cellulosic plastic, of sufficient strength to withstand the pressures involved, which may be up to about 150 psi or more.

The sleeve 20 is of generally elongated rectangular cross-sectional shape with top and bottom walls 26 and 28 and side walls 30 and 32. The sleeve is open at one end for receiving the insert member 22, and closed at the other end by end wall 36. A groove 34 is provided along the inside surface of each of the side walls 30 and 32 for slidably receiving the edge of the insert member. A raised cylindrical boss 38 is provided interior of the end wall 36, and has a cylindrical bore 40 for receiving in sealed relationship the outlet port 16 of the insert member 22.

The open end of the sleeve 20 is closed by the separate cap 24, which includes the inlet port 14 molded integrally therewith to communicate with the inside of the otherwise sealed sleeve. A pair of plastic legs 42 extend from the inside surface of the cap to brace against the insert member 22 to keep the outlet port 16 tightly fitted within the cylindrical bore 40. A resilient O-ring seal 44 around the outlet port 16 helps to provide a better seal against the surface of the bore 40, although the outlet port 16 could also be sealed within the bore 40 by solvent bonding, sonic welding or the like.

The filter cartridge of insert member 22 comprises a thin plastic internal loop 46 of preferably oval shape, with the filter membranes 12 and 18 peripherally sealed in a parallel relationship against a flat mounting surface on each side of the loop. The integral outlet port 16, communicates through one end of the loop with the narrow space between the membranes. The thickness of the loop may be varied, depending on the material of the filter membranes 12 and 18, so that the parallel membranes can stretch or flex to a mutually supporting position, usually half the thickness of the insert, without exceeding their elastic limit. In addition, the inside edge of the loop is gently curved, at 48, to conform to the deflecting membranes so as not to impart any additional stresses or stress concentrations in the membranes.

As noted earlier, the use of two microporous filter membranes 12 and 18 in a parallel flow relationship, analogous to a parallel electrical circuit, with liquid being divided to pass through one or the other of the membranes and then recombined in the space therebetween before exiting through outlet port 16, provides a relatively large filter surface area for a high volume of liquid flow through the filter assembly. Each of the filter membranes used in the assembly is of substantially the same dimensions and pore size, which must be sufficiently small to remove particulate from the filtering liquid. Usually the mean pore size for the filter membranes will be substantially less than 1 micron, preferably in the range between about 0.05 and 0.15 microns, inclusive.

Filter membranes of the type described above for filtering liquids are usually hydrophilic in nature. That is, when wetted by the filtering liquid, they become substantially impermeable to gas bubbles which may be entrained in the fluid stream. The so-called "bubble point" is the measure of a membrane's resistance to the passage of gas bubbles. It is dependent on a variety of factors including the membrane material and pore size, but for purposes of the present application, "bubble point" is generally defined as the fluid pressure at which gas bubbles can be forced through a wetted hydrophilic filter membrane. For hydrophilic membranes within the pore size range set forth above, the bubble point may be in the range of from about 100 psi to about 250 psi. The selection of a membrane with a bubble point above the transient high pressures which may be encountered in the administration system has the significant advantage of preventing air or gas bubbles entrained in the fluid stream from passing to the patient, even when a transient high pressure condition occurs.

In the preferred embodiment, the microporous hydrophilic membranes 12 and 18 are sealed on either side of the insert member 22 in a closely spaced geometrically parallel, as well as parallel flow relationship. In accordance with one aspect of the present invention, the material for the filter membranes is selected to have a modulus of elasticity sufficiently high to prevent flexure of the membranes to the mutually supportive position, shown in FIGS. 5 and 6, under normal liquid flow pressures of about 0 to 20 psi, but is low enough to permit the filter membranes to stretch or flex to the mutually supporting position when a selected high fluid pressure occurs, e.g., 100 psi, which may generated during a syringe injection.

Along with the selection of a material having the desired modulus of elasticity, the spacing between the membranes 12 and 18, i.e., the thickness of the insert 22, must be chosen so that the longitudinal and lateral stresses imposed on the membranes when they flex or stretch to the mutually supportive position, midway between them, do not exceed the elastic limit for the selected material. Thus, when transient high pressure conditions occur, the membranes 12 and 18 will flex a small amount, to the mutually supportive position which prevents further flexure, and will then return to the spaced-apart position after the pressure is relieved.

One example of a hydrophilic microporous membrane which may be employed in connection with the present invention is made of mixed esters of cellulose, has a 0.1 micron mean pore size, a bubble point of about 250 psi, and a modulus of elasticity of about $1.2 \times 10^5$ psi. For such filter membranes, the insert member 22 should be sufficiently thick to provide a spacing of from about 0.050 to about 0.060 inches between the membranes. Because each deflects only one-half of the spacing between them, each membrane must only deflect from about 0.025 to about 0.030 inches before reaching the mutually supporting position.

When the membranes 12 and 18 are in direct supporting contact in the mutually supportive position, it is also apparent that they substantially prevent flow of liquid through the outlet 16, effectively acting as a valve, preventing liquid flow when a high pressure condition occurs. When the filter assembly 10 is downstream of the pressure generating source, e.g. syringe or IV pump, this valving feature prevents exposure of the patient to possibly detrimental high fluid pressures.

Although the preferred embodiment of the present invention uses a pair of facing membranes which permit relatively large flow rates through the filter assembly, it is consistent with the present invention to use only one membrane, spaced closely adjacent a co-extensive support surface, for example, a wall of the filter assembly housing downstream of the membrane so that when experiencing high pressures, the membrane would flex against the wall rather than against a facing membrane. In either case, the spacing between the membranes or between the membrane and the support surface are calculated so that the flexure needed for the membrane to rest substantially fully against the support surface does not exceed the elastic limit for the membrane.

In summary, in accordance with the present invention a unique membrane filter assembly is provided which is easy to assemble, provides relatively high flow rates and does not require additional reinforcing structure or assembly steps to protect the membrane against transient high pressures. In addition to acting as a valve to protect the patient or pressure-sensitive downstream apparatus against high transient pressures, hydrophilic membranes with high bubble points may also be used to prevent injection of gas or air bubbles into the patient.

Although the present invention has been described in terms of the preferred embodiment, it is intended to include those equivalent structures, some of which may be apparent upon reading this specification and others which may be revealed only after some study.

What is claimed is:

1. A filter assembly comprising:
   housing means defining an interior fluid passageway and inlet and outlet opening means communicating therewith;
   a pair of spaced-apart facing co-extensive microporous filter membranes carried within said fluid passageway in parallel flow relationship to filter liquid passing therealong at a selected pressure;
   said membranes having a modulus of elasticity to maintain said membranes spaced from each other at a selected normal flow pressure and to permit said membranes to flex to a mutually supporting position, where each membrane substantially fully rests against the other membrane at a flow pressure higher than said selected flow pressure,
   said membranes being spaced apart a selected distance which is sufficiently small that the stress in each of said flexed membranes does not exceed its elastic limit when resting substantially fully against said other membrane.

2. A filter assembly in accordance with claim 1 comprising spacing means disposed between said facing membranes only along the peripheral edges thereof.

3. A filter assembly in accordance with claim 2 wherein said spacing means includes an inside edge portion to conform to said membranes when they deflect under said higher fluid pressure.

4. A filter assembly in accordance with claim 2 wherein said spacing means extends continuously around the peripheral edges of said membranes and includes outlet opening means therethrough to permit flow from the space between said membranes.

5. A filter assembly in accordance with claim 2 wherein said housing includes a sleeve portion, said spacing means and said membranes comprising a unit telescopically received within said sleeve portion.

6. A filter assembly in accordance with claim 5 wherein said sleeve portion includes an open end and a closed end, said closed end having an outlet port therethrough, said outlet opening in said spacing means being in sealed communication with said outlet port in said closed end portion of said sleeve.

7. A filter assembly in accordance with claim 1 wherein said membranes are spaced between about 0.050 and 0.060 inches apart.

8. A filter assembly in accordance with claim 1 wherein said filter membranes is hydrophilic and has a bubble point greater than said higher pressure.

9. A filter assembly in accordance with claim 1 wherein said filter membranes have a mean pore size between about 0.05 and 0.15 microns.

* * * * *